United States Patent [19]

Grabitz

[11] Patent Number: 4,695,549

[45] Date of Patent: Sep. 22, 1987

[54] METABOLICALLY ACTIVE PREPARATIONS OBTAINED FROM YEAST OF ANY TYPE

[75] Inventor: Ernst B. Grabitz, Casatenovo, Italy

[73] Assignee: Hasunor A.G., Lugano, Switzerland

[21] Appl. No.: 607,563

[22] Filed: May 7, 1984

[30] Foreign Application Priority Data

May 20, 1983 [CH] Switzerland .......................... 2787/83

[51] Int. Cl.$^4$ .......................... C07G 17/00; C12N 1/06; C12R 1/85; A61K 35/78
[52] U.S. Cl. .................................. 435/267; 435/259; 435/940; 424/195.1; 514/783
[58] Field of Search ................ 530/371, 824; 435/272, 435/940, 267, 259; 424/195.1; 426/60; 514/783

[56] References Cited

U.S. PATENT DOCUMENTS 4,218,481  8/1980  Chao et al. ..................... 435/267 X
4,313,934  2/1982  Kitamura et al. ............... 530/371 X Primary Examiner—Esther M. Kepplinger
Assistant Examiner—Shawn P. Foley
Attorney, Agent, or Firm—Stevens, Davis, Miller & Mosher

[57] ABSTRACT

A process for obtaining a sterile, apyrogenic product for promoting oxidative phosphorylation and suitable for therapeutic or cosmetic compositions, starting from yeast, in which any type of yeast is subjected to a process of plasmolysis, followed by treatment with proteolytic enzymes and then with diamine oxidase, after which the proteins present in the solution are precipitated by alcohols, the solution pH is stabilized, and the solution concentrated at low temperature under vacuum.

9 Claims, No Drawings

METABOLICALLY ACTIVE PREPARATIONS OBTAINED FROM YEAST OF ANY TYPE

The oxidative phosphorylation process is of fundamental importance for all aspects of cell life in aerobic organisms, because it represents the main source of utilisable energy.

The phenomenon known as oxidative phosphorylation is essentially a process which proceeds in the chondriosomes, and is connected with the formation of ATP phosphate groups "of high energy level" by the yielding of free energy, and in which energy transfer takes place in stages by electron transfer during the respiratory process.

The term "of high energy level" signifies those compounds possessing a high group transfer potential (6–14 Kcal/mole instead of 3–5 Kcal/mole for normal phosphoric esters).

A vast literature is available regarding oxidative phosphorylation inhibitors (decoupling, Pasteur effect, antibiotics), whereas oxidative phosphorylation activators are not known. Only organ extracts from the blood and liver are known, however in these the discernable effects are very modest, and are mostly due to extraneous substances which in practice increase oxygen consumption during respiration, but not ATP production by the cell.

The subject matter of the present invention is the production of preparations active in intermediary metabolism, starting from suitably treated yeast.

In the preparation and treatment of the yeast extract according to the present invention, the basic problem is the separation of those cell components which are undesirable because they partly exercise an inhibition action, but without the activators being damaged by this treatment.

Operating in a sterile, apyrogenic environment is a necessity for the process. Complete elimination of the proteins, including the removal of substances of histamine type, is also an essential part of the preparation process.

The yeast treatment process according to the present invention comprises the following essential operations:
1. Plasmolysis and homogenisation at a temperature less than 0° C.
2. Proteolysis by proteolytic enzymes
3. Treatment with enzymes able to split the histamine-type products, in particular diamine oxidase
4. Treatment with alcohols in order to eliminate proteins
5. pH adjustment
6. Concentration under vacuum.

In stage 1, in order to obtain plasmolysis, the substance is treated with water, and the mixture then kept at a temperature of the order of −20° C. for some days.

In stage 2, proteolytic enzymes such as pronase, trypsin and ox pancreas are used in order to eliminate the proteins.

Stage 3 consists of eliminating histamine-type substances using diamine oxidase at pH 6.5–8.0.

Fractional precipitation with alcohols eliminates residual proteins (stage 4). The fractional precipitation is carried out using a mixture of mono and polyvalent alcohols comprising:
(a) a monovalent aliphatic alcohol of 2–6 C atoms;
(b) two or more polyvalent alcohols, possibly partly esterified, containing at least 3 C atoms (without counting any ester groups), and present in a total quantity of 0.5%–30% by weight with respect to the monovalent aliphatic alcohol, they being preferably chosen from glycerin, sorbitol, mannitol, inositol and pentaerythritol acetate;
(c) one or more arylaliphatic alcohols of 7–12 C atoms, in a total quantity corresponding to 0.05%–5% by weight with respect to the monovalent aliphatic alcohol.

The pH of the solution obtained after removing those protein substances insolubilised in the alcohol treatment of stage 4 is adjusted by means of buffer solutions of pH 6.5–7.

Suitable buffer solutions are for example those based on citric, lactic or ascorbic acid, or N-alkylsubstituted hexamines.

The solution of stabilised pH is finally concentrated under vacuum at low temperature of the order of −10° C. or less, until a nitrogen content in the concentrate of at least 1.4 mg/ml is obtained (stage 6).

Elimination of the proteins and substances of histamine type is particularly important when the final product is used for injectable therapeutic compositions.

A bacteriostatic agent in a percentage compatible with the final product to be obtained must be added to the initial yeast suspension. Any bacteriostatic agent can be used which is compatible with the final destination of the prepared product. In particular, parahydroxyalkylbenzoates are suitable.

The active preparations obtained according to the present invention have a very high stability with time which means that they can be conveniently used in practice in many forms and by various methods of application.

As stated, these active preparations produce an activation of the metabolic oxidation processes which can be represented by the "respiration factor". It has been found that this respiration factor in the case of the active preparations according to the invention has values of between 2.5 and 4. As a comparison, this factor reaches 1.5 in blood extracts and 1.2 in placenta extracts.

The respiration factor of the products prepared according to the invention was determined by the Warburg method described by A. Kleinzeller in "Manometrische Methoden" VEB G. FRISCH Verlag, Jena 1965.

The metabolically active products prepared according to the invention, in the form of a solution, are practically free from toxicity. The LD in the mouse is in fact greater than 20 g/kg.

Observations carried out in mice treated over a time of between 1 minute and 24 hours show that the reflexes, tone, coordination, emotion, reactivity, and the reflexes related to the central nervous system are not altered with respect to their normal state.

The products in question cause no cutaneous irritation with the normally used tests in accordance with "Appraisal of the safety of chemicals in foods, drugs and cosmetics" of the F.D.A.

Cutaneous toxicity and eye irritability were determined by the Draize method.

The absence of histamine products is confirmed by the cat test (U.S.P. Pharmacopea XX page 890 (101)).

The product can be administered by intramuscular, intraperitoneal or intravenous injection, or alternatively orally or topically.

Intravenous administration favourably influences circulatory disturbances, in particular of the peripheral, overall and local circulation. It is particularly useful in acute or chronic ischemia.

Parenteral administration is particularly useful in mucosa regeneration, for example in the case of ulcers and burns.

Application of the product accelerates tissue formation in plastic surgery operations.

This effect is exercised on all types of tissue, including osseous.

It also suppresses tissue irritation due to therapeutic radiation treatment.

The product according to the invention improves skin structure, and can therefore find useful application in cosmetics.

In the basic epidermis layer, new cells are continuously formed which displace those previously formed and force them outwards towards the skin surface (desquamation).

Under normal skin conditions, the epidermis is renewed in a period of one month, and from the basic layer where it is in contact with the dermis in order to assume nutriment it moves through the "compact" layer towards the "loose" layer where segregation occurs. In this process the skin cell passes through the cell stages pertaining to the granular layer, spinous layer and finally the horny layer (keratin), this cell being flat, dry and dead. It has now been found that by energetically rubbing the new product on to the skin at a concentration of 4%-5% in a suitable ointment, a greater number of new cells is formed in the dermis, with the removal of the "disjointed" layer in the basic layer, and these cells are characterised by being particularly hydrated, rich in cytoplasmatic liquid, and disposed closely next to each other. The product is therefore very useful for cosmetic applications.

EXAMPLE

Preparation of metabolically active yeast extract

The starting material is yeast of the Saccharomyces species, for example beer or bread yeast.

The yeast is mixed with 5 parts of distilled water containing 0.1% by weight of methyl-parahydroxybenzoate, and the mixture is kept at −20° C. for more than 8 days. After this time, it is homogenised at −20° C. and the pH is adjusted to its initial value. The mixture is then subjected to the action of proteolytic enzymes at 36.5° C. Trypsin and ox pancreas are used, and the system is kept at pH 8 and maintained at said temperature for a minimum of 70 hours and a maximum of 120 hours. The unreacted proteins and cell residues are separated by conventional methods, for example by filtration using filter beds, or preferably by centrifuging. At this point a solution is obtained. In order to remove histamine-type substances from this latter, it is treated with diamine oxidase at pH 6.2–8.0 until the histamine compounds disappear.

The solution is then subjected to fractional precipitation by adding a mixture of alcohols in order to eliminate residual proteins.

Said mixture consists of 10 parts by weight of ethanol, 0.2 parts by weight of glycerin, 0.001 parts by weight of phenylpropyl-alcohol, 0.02 parts by weight of benzyl alcohol and 0.0005 parts by weight of pentaerythritol acetate.

When precipitation is complete, the mixture is filtered or centrifuged, and the solution is adjusted to pH 7 by means of a buffer solution based on citric, ascorbic or lactic acid and N-alkylglucamine.

The solution is then concentrated at −15° C. and under a vacuum of 1–20 mmHg until a nitrogen concentration of 1.4 mg/ml is attained in the final preparation.

This latter is in the form of a solution stable with time, and having a respiration factor of at least 3.5–4.

I claim:

1. A process for obtaining a sterile, pyrogen-, histamine- and protein-free solution containing at least 1.4 mg/ml of nitrogen, useful as a promoter of oxidative phosphorylation, which comprises the steps:

(a) plasmolyzing an aqueous dispersion of yeast at a temperature of less than 0° C.,
    (b) adding a proteolytic enzyme,
    (c) adding a diamine oxidase in order to remove histamine,
    (d) adding a mixture of a monovalent $C_2$–$C_6$ aliphatic alcohol with two or more polyvalent alcohols containing at least 3 carbon atoms, to precipitate protein,
    (e) separating liquid by filtration or centrifugation,
    (f) adding a buffer solution to stabilize the separated liquid at pH 6–7, and
    (g) concentrating the stabilized liquid under vacuum said liquid being a sterile, pyrogen-, histamine- and protein-free solution containing at least 1.4 mg/ml of nitrogen.

2. A process according to claim 1, wherein the polyvalent alcohol is present in an amount 0.5–30% by weight of the monovalent alcohol.

3. A process according to claim 1, wherein the polyvalent alcohol is partially esterified.

4. A process according to claim 1, wherein the polyvalent alcohol is selected from the group consisting of glycerin, sorbitol, mannitol, inositol and pentaerythritol bisacetate.

5. A process according to claim 3, wherein the polyvalent alcohol is pentaerythritol bisacetate.

6. A process according to claim 1, wherein to the monovalent aliphatic alcohol and polyvalent alcohols mixture is added an aryl aliphatic alcohol having 7–12 carbon atoms in an amount corresponding to 0.05–5% by weight with respect to the monovalent alcohol.

7. The solution prepared by the process of claim 1.

8. The solution according to claim 7, further comprising a bacteriostatic agent.

9. The solution according to claim 8, wherein the bacteriostatic agent is methyl p-hydroxybenzoate.

* * * * *